(12) United States Patent  
Kitano

(10) Patent No.: US 8,956,279 B2
(45) Date of Patent: Feb. 17, 2015

(54) CAMERA MODULE FOR ENDOSCOPE AND ENDOSCOPE

(71) Applicant: Fujifilm Corporation, Tokyo (JP)

(72) Inventor: Ryou Kitano, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 224 days.

(21) Appl. No.: 13/623,711

(22) Filed: Sep. 20, 2012

(65) Prior Publication Data

US 2013/0085328 A1   Apr. 4, 2013

(30) Foreign Application Priority Data

Sep. 30, 2011   (JP) ................................. 2011-216676

(51) Int. Cl.
*A61B 1/00* (2006.01)
*A61B 1/05* (2006.01)
(52) U.S. Cl.
CPC ......... *A61B 1/00096* (2013.01); *A61B 1/00126* (2013.01); *A61B 1/051* (2013.01)
USPC ............................. 600/110; 600/109; 600/112
(58) Field of Classification Search
CPC .. A61B 1/00096; A61B 1/00126; A61B 1/05; A61B 1/051; A61B 1/053; A61B 1/00121; A61B 1/00128
USPC .......................................... 600/110, 109, 132
See application file for complete search history.

(56) References Cited

U.S. PATENT DOCUMENTS

| | | | |
|---|---|---|---|
| 2005/0197536 A1* | 9/2005 | Banik et al. | 600/179 |
| 2006/0173242 A1* | 8/2006 | Navok et al. | 600/133 |
| 2007/0055104 A1* | 3/2007 | Kumei et al. | 600/176 |
| 2007/0191684 A1* | 8/2007 | Hirata | 600/179 |
| 2008/0225134 A1* | 9/2008 | Amling et al. | 348/222.1 |
| 2009/0284649 A1* | 11/2009 | Pease et al. | 348/376 |
| 2010/0188492 A1* | 7/2010 | Jacobsen et al. | 348/68 |
| 2010/0210905 A1* | 8/2010 | Takeuchi et al. | 600/110 |
| 2010/0305400 A1* | 12/2010 | Onoda et al. | 600/104 |

(Continued)

FOREIGN PATENT DOCUMENTS

| | | |
|---|---|---|
| JP | 5-261064 A | 10/1993 |
| JP | 9-146011 A | 6/1997 |

(Continued)

OTHER PUBLICATIONS

Notice of Reason(s) for Rejection dated Jul. 24, 2013, with English translation.

*Primary Examiner* — John P Leubecker
*Assistant Examiner* — Arnaldo Torres Diaz
(74) *Attorney, Agent, or Firm* — McGinn IP Law Group, PLLC

(57) ABSTRACT

One end of a cable connecting fitting is fixed to a transmission cable. After a locking claw provided on the other end of the cable connecting fitting is locked to the tip surface of a mounting tube portion of a prism holder, the mounting tube portion and the cable connecting fitting are fixed to each other. An image area sensor is close to the inner circumferential surface of a distal end hard portion, and a camera module is disposed in the distal end hard portion. The cable connecting fitting can be disposed at a free space between the inner circumferential surface of the distal end hard portion and the image area sensor. The size of the cable connecting fitting can be increased within a range of the free space, connection strength is secured, and separation of the prism or junctions and rupture of the transmission cable can be suppressed.

17 Claims, 15 Drawing Sheets

(56) References Cited

U.S. PATENT DOCUMENTS

| | | | |
|---|---|---|---|
| 2011/0021872 A1* | 1/2011 | Kumei | 600/104 |
| 2011/0092769 A1* | 4/2011 | Kokubo | 600/109 |
| 2011/0254938 A1* | 10/2011 | Asada et al. | 348/76 |
| 2012/0206583 A1* | 8/2012 | Hoshi et al. | 348/76 |
| 2012/0310043 A1* | 12/2012 | Hu et al. | 600/109 |
| 2013/0137924 A1* | 5/2013 | Iwasaki et al. | 600/109 |
| 2013/0182099 A1* | 7/2013 | Nakamura | 348/86 |

FOREIGN PATENT DOCUMENTS

| | | | |
|---|---|---|---|
| JP | 2004-283486 A | | 10/2004 |
| JP | 2008-79823 A | | 4/2008 |
| JP | 2008079823 A | * | 4/2008 |
| JP | 2008-118568 A | | 5/2008 |
| JP | 2010-69186 A | | 4/2010 |
| JP | 2010069186 A | * | 4/2010 |

* cited by examiner

CAMERA MODULE FOR ENDOSCOPE AND ENDOSCOPE

BACKGROUND OF THE INVENTION

1. Field of the Invention

The present invention relates to a camera module for an endoscope and an endoscope.

2. Description of the Related Art

For example, an endoscope includes an insert unit that is inserted into the body of a patient. The insert unit includes a distal end hard portion, a curved portion, and a soft portion in this order from the tip. Moreover, an observation window, an illumination window, a forceps outlet, and an air and water supply nozzle are provided in the tip surface of the distal end hard portion. In addition, in the inner surface of the distal end hard portion, a camera module is mounted at a position corresponding to the observation window and a light guide is mounted at a position corresponding to the illumination window respectively. The curved portion is configured so as to connect a plurality of joint ring units and cause the distal end hard portion to be directed toward a desired direction through a wire operation. The soft portion has a length of about 1 m to 2 m for making the distal end hard portion reach a desired observation portion of a subject.

The camera module includes a photographic lens unit and an imaging unit. The photographic lens unit is configured to accommodate a plurality of lenses in the housing. The imaging unit includes an image area sensor such as a CCD or a CMOS that converts an optical image imaged by the photographic lens unit to image signals. The image area sensor is connected to a transmission cable via a circuit substrate such as a flexible substrate or a sub-board. In addition, electronic components for driving the image area sensor are mounted to the flexible substrate or the sub-board. Signals from the imaging unit are sent to an image processor via the flexible substrate or the sub-board and the transmission cable. The image processor performs image processing of the signals and displays images such as a lesion on a monitor.

The transmission cable that sends the signals from the imaging unit to the image processor is configured of a compound multicore cable. Since the transmission cable is inserted over the entire length of the insert unit, the transmission cable is strongly pushed and pulled whenever the insert unit is looped or curved. If the transmission cable is pulled into the insert unit, junctions of the substrate may be separated or the transmission cable may be cut.

In order to avoid the separation or the cutting, various suggestions have been made. For example, in an endoscope disclosed in JP1993-261064A (JP-H05-261064A), a transmission cable is soldered to one end side of a flexible substrate, the flexible substrate is bent in a U form so as to surround the soldered transmission cable, the periphery of the bent flexible substrate is covered using a shield tape and an insulating tape, and epoxy-based adhesive is filled into the inner space of the tapes and is hardened so as not to be deformed. In addition, since the circuit substrate of the side in which the transmission cable is fixed is fixed to a connection tube through a fixing screw via a pressing plate, even when the transmission cable is strongly pushed and pulled, the circuit substrate does not move, and torsion or an inclining force that is applied to the circuit substrate from the transmission cable is absorbed by the circuit substrate having flexibility and is not transmitted to the image area sensor and an object optical system.

In a camera module disclosed in JP1997-146011A (JP-H09-146011A), a sealing material covers a connection unit between a flexible substrate and a transmission cable and is hardened.

In a camera module disclosed in JP2008-118568A, a reinforced frame that accommodates an image area sensor and an electronic component mounting unit of a flexible substrate is provided, and an adhesive material is filled into the inner side of the reinforced frame. In addition, the tip portion of a transmission cable that is soldered to the flexible substrate and the reinforced frame are covered using a heat shrinkable tube, and an adhesive material is filled into the inside of the tube and is sealed.

In a camera module disclosed in JP2004-283486A, a mechanism that changes a focal distance of a photographic lens is provided, and the focal distance can be switched between a general observation and an enlargement observation. In such a camera module, a photographic lens unit and an imaging unit lens are configured so as to be separated and are fixed to the photographic lens unit via a prism holder of the imaging unit and integrated with each other, and the camera module is thus configured.

SUMMARY OF THE INVENTION

In the camera module disclosed in JP1993-261064A (JP-H05-261064A), since the circuit substrate is fixed to the connection tube using the fixing screw, there is a disadvantage in that complicated operations are required. In the camera module disclosed in JP1997-146011A (JP-H09-146011A), the force that pushes and pulls the transmission cable is transmitted to the junction between the cable and the flexible substrate or the flexible substrate. The force that is transmitted to the flexible substrate is applied to the soldered portion between the transmission cable and the flexible substrate, the junction between the flexible substrate, and the image area sensor, and the like, and thereby, there is a concern that separation or damage may occur at locations that are weakened due to the force.

In the camera module disclosed in JP2008-118568A, since the image area sensor is accommodated in the inner portion of the reinforced frame, the size of the image area sensor is affected by the size of the reinforced frame. Demands on an endoscope are also being diversified to such as having a higher quality image, a reduced diameter, and compatibility with an autoclave, and according to this, the image area sensor and the peripheral parts are also becoming diversified and complicated. If functions are increased in the image area sensor and the peripheral parts and the sizes thereof are increased, the size of the reinforced frame which accommodates the image area sensor and the peripheral parts is also increased. Thereby, the diameter of the distal end hard portion of the insert unit of the endoscope is thickened, and there is a disadvantage in that a burden on a patient is increased.

In the camera module disclosed in JP2004-283486A, the prism is fixed via the prism holder, and the photographing element, the circuit substrate, and the like are fixed to the fixed prism. Moreover, the transmission cable is connected to the circuit substrate. Thereby, a pulling force acts on the connection unit of the transmission cable, which becomes a cause of breaking of the wire. Moreover, the entire surfaces of the prism and the image area sensor are adhered. However, since an opening is formed on the prism holder in order to make light from the photographic lens unit enter an incident surface of the prism, the entire surface adhesion of the prism holder is not possible. Therefore, the peripheral edge of the incident surface and the holder are only adhered to each other, and if the transmission cable is pulled, there is a concern that the prism may be separated from the adhered portion.

The present invention has been made in view of the above-mentioned problems and an object of the present invention is to provide a camera module for an endoscope and an endoscope capable of suppressing occurrence of damage to parts such as a transmission cable, a flexible substrate, and an image area sensor, and occurrence of separation of junctions of these or separation between a prism holder and a prism even when the transmission cable is strongly pushed and pulled, and capable of reducing a burden on a patient by reducing the diameter of a distal end hard portion.

In order to achieve the object, a camera module for an endoscope of the present invention includes: a photographic lens unit that includes a photographic lens and a housing holding the photographic lens; a prism that includes an incident surface to which photographing light from the photographic lens is incident, a reflecting surface at which the photographing light incident to the incident surface is reflected, and an emitting surface that emits the photographing light reflected at the reflecting surface; a prism holding frame that includes a mounting tube portion mounted on one end of the housing, an opening through which incident light of the incident surface of the prism passes, and a prism fixing surface to which a peripheral edge of the incident surface of the prism is fixed; an image area sensor that is mounted on the emitting surface of the prism; a circuit substrate that drives the image area sensor; a transmission cable that includes wires connected to the circuit substrate and an outer cover that bundles and protects the wires; and a cable connecting fitting which is close to the image area sensor and disposed so as to be parallel to the image area sensor, and in which one end is fixed to the outer cover of the transmission cable and the other end is mounted on the mounting tube portion. Here, disposing to be parallel includes being approximately parallel.

In addition, the other end of the cable connecting fitting may include a locking claw locked to the tip surface of the mounting tube portion. Moreover, the other end of the cable may be fixed to the mounting tube portion. In addition, the cable connecting fitting may include a protrusion for reinforcement that is provided from the one end to the other end. The cable connecting fitting may include a spring portion that is bent in a width direction perpendicular to the longitudinal direction which extends from the one end to the other end.

In addition, in the present invention, in an endoscope that includes a cylindrical distal end hard portion on which the camera module for an endoscope is mounted, the image area sensor is disposed so as to be close to the cylindrical inner circumferential surface in the distal end hard portion.

According to the present invention, since the cable connecting fitting in which one end is fixed to the outer cover of the transmission cable and the other end is mounted to the mounting tube portion of the prism holding frame is provided, when the insert unit of the endoscope is repeatedly bent and the transmission cable is pulled, the pulling force is transmitted to the prism holding frame due to the cable connecting fitting. Therefore, the pulling force does not act on the prism, a circuit substrate, and the like, and separation of the prism, breaking of wires, or the like does not occur. Moreover, the image area sensor, which is mounted on the emitting surface of the prism and is disposed in the direction perpendicular to a photographing optical axis, is disposed so as to be close to the cylindrical inner circumferential surface in the distal end hard portion. Thereby, the cable connecting fitting can be disposed in a free space between the inner circumferential surface of the distal end hard portion and the image area sensor. The size of the cable connecting fitting can be increased within a range of the free space, connection strength is secured, and separation of the prism or junctions and rupture of the cable can be suppressed.

DESCRIPTION OF THE PREFERRED EMBODIMENTS

Figure 1:
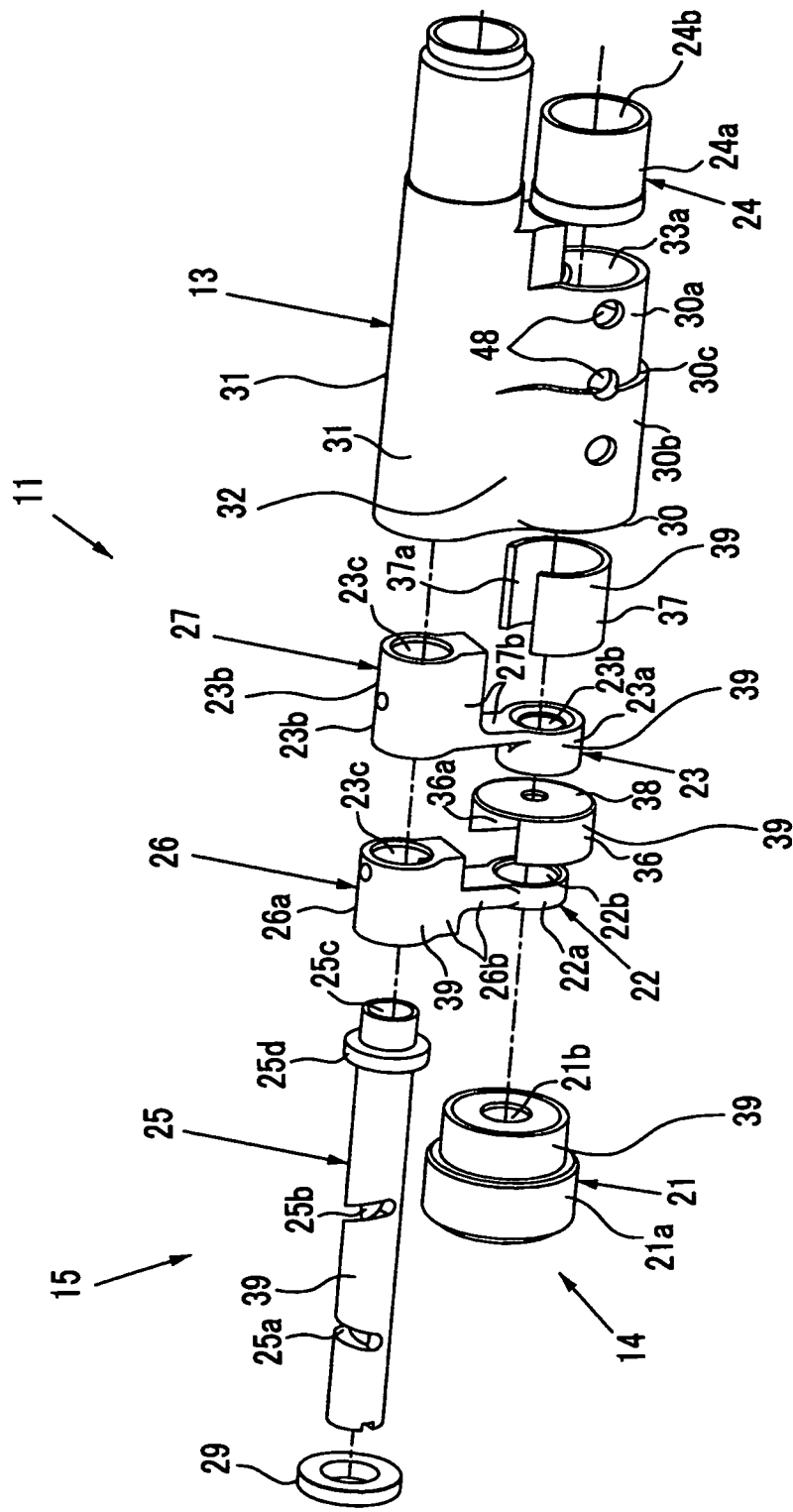
FIG. 1 is a perspective view in which a photographic lens is shown in an exploded manner.
Figure 2:
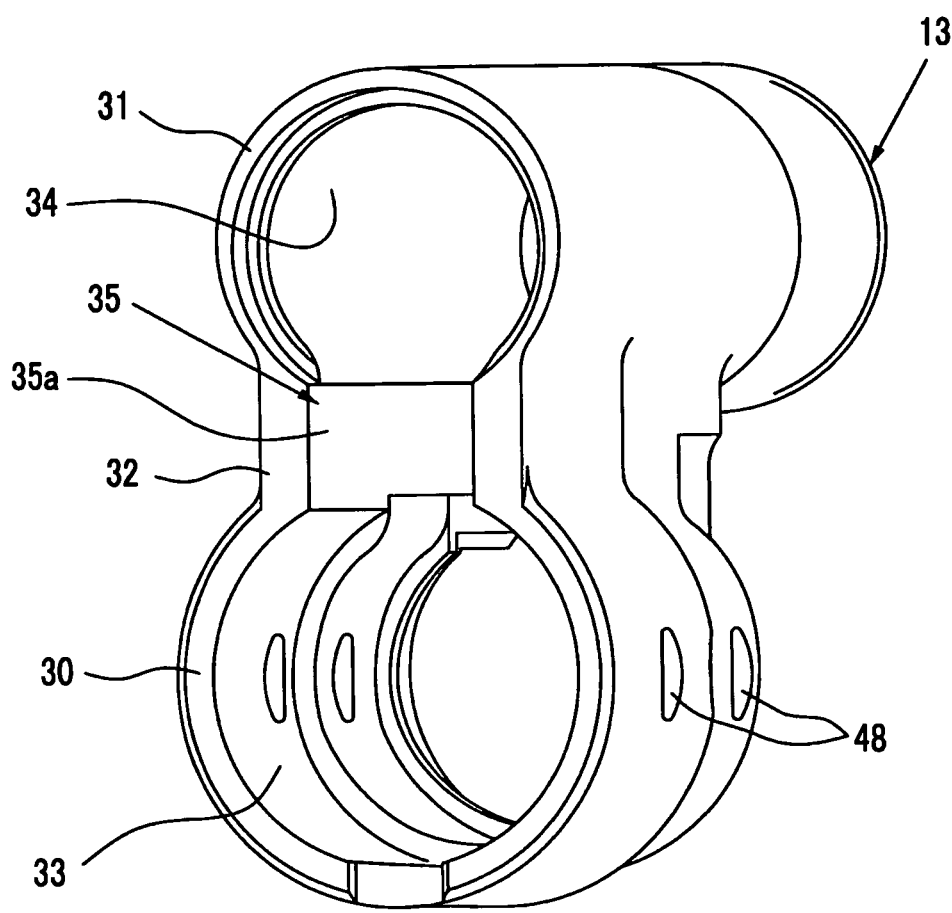
FIG. 2 is perspective view when a housing is obliquely viewed from the front.
Figure 3:
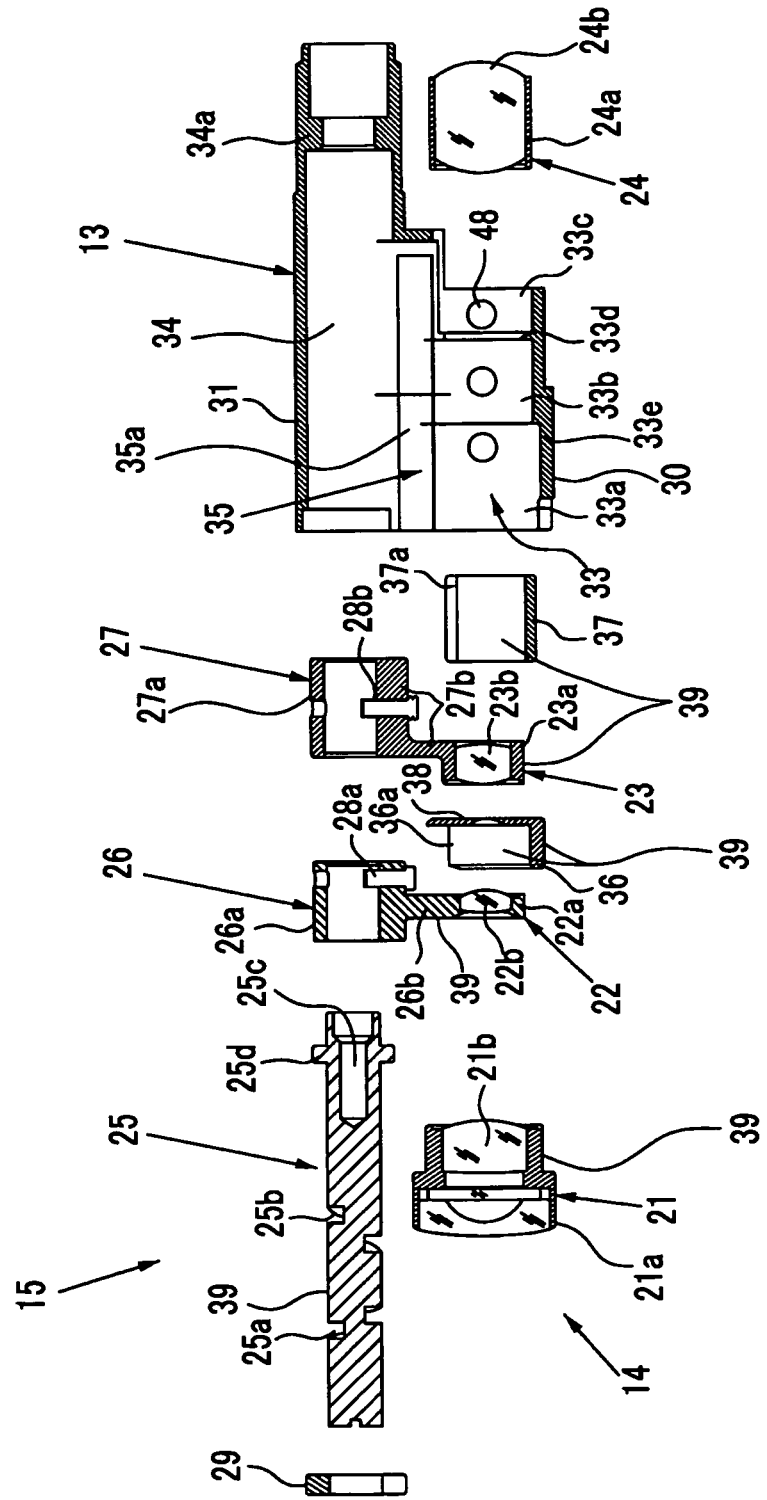
FIG. 3 is a cross-sectional view in which the photographic lens unit is shown in an exploded manner.

As shown in FIGS. 1 to 3, a photographic lens unit 11 includes a housing 13, and a photographic lens 14 and a lens movement unit 15 that are accommodated in the housing 13.

A first fixing lens 21, a first movable lens 22, a second movable lens 23, and a second fixed lens 24 are disposed in an optical axis direction, and thereby, the photographic lens 14 is configured. Each of the fixed lenses 21 and 24 and each of the movable lenses 22 and 23 include lens frames 21a to 24a, and a single lens main body or a plurality of lens main bodies 21b to 24b that are held by the lens frames 21a to 24a.

The lens moving unit 15 includes a cam shaft 25 and, a first lens moving frame 26 and a second lens moving frame 27 that slidably move on the cam shaft 25. The lens moving unit 15 moves the movable lenses 22 and 23 in the optical axis direction, and thereby, a focal distance of the photographic lens 14 is changed, and variable magnification photographing is possible.

A first tube unit 30 and a second tube unit 31 are arranged in a direction perpendicular to a tube axial direction and are connected through a connection unit 32, and thereby, the housing 13 is configured. As shown in FIG. 2, the outer diameter of the second tube unit 31 is slightly smaller than the outer diameter of the first tube unit 30, and the housing is formed in a figure of eight when viewed from the front. A photographic lens accommodating hole 33 is formed on the first tube unit 30, and the photographic lens 14 is accommodated in the hole 33. A lens moving unit accommodating hole 34 is formed on the second tube unit 31, and the lens moving unit 15 is accommodated in the hole 34. As shown in FIG. 3, a locking ring 34a is formed so as to protrude in the lens moving unit accommodating hole 34. Moreover, a slide hole 35 that connects the photographic lens accommodating hole 33 and the lens moving unit accommodating hole 34 is formed in the connection unit 32.

Figure 4:
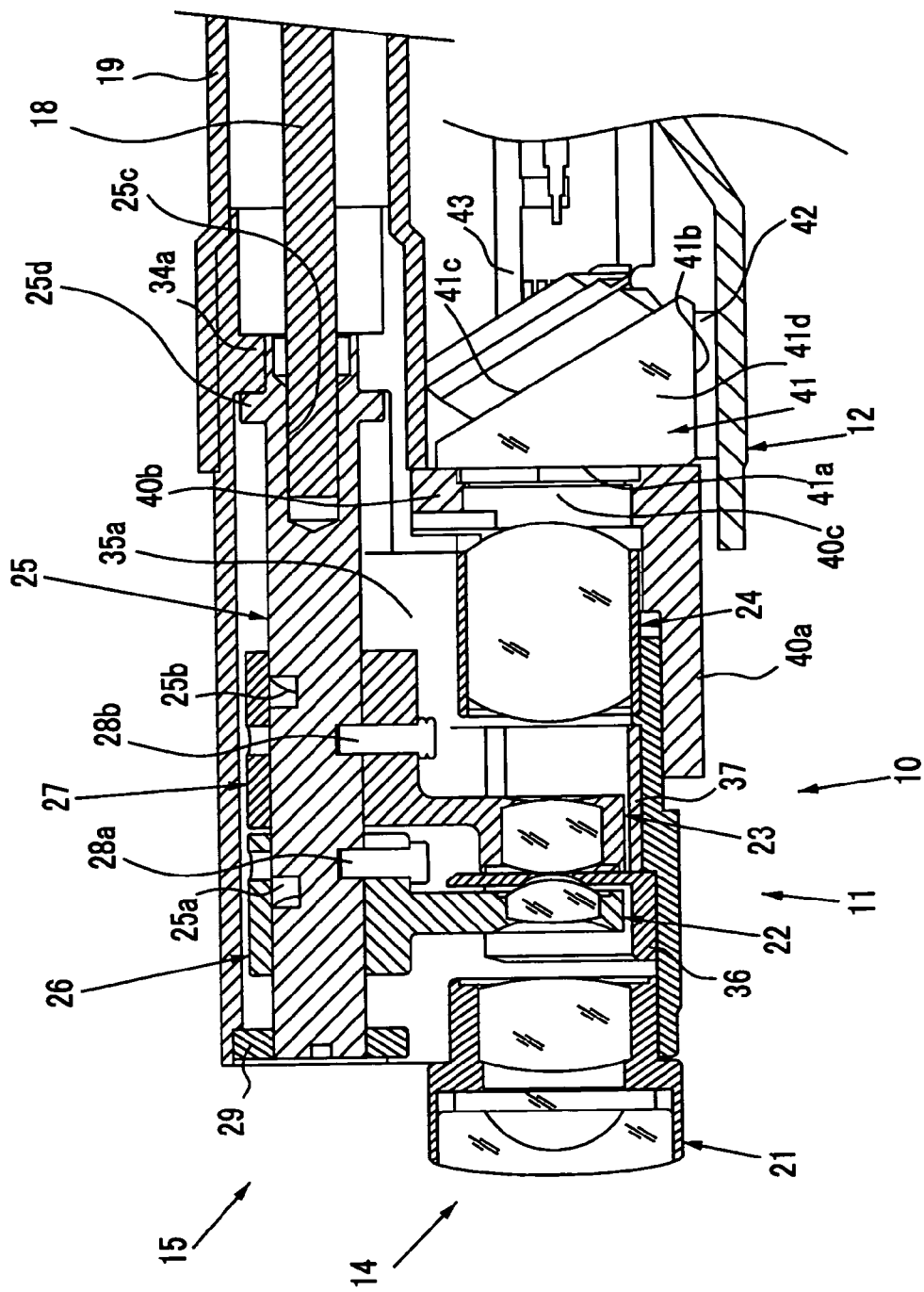
FIG. 4 is a main portion cross-sectional view of a camera module at a standard position.

As shown in FIGS. 1 and 3, the cam shaft 25 includes two cam grooves 25a and 25b on the outer circumferential surface, a wire connection hole 25c along the shaft center at the rear end, and a locking flange 25d on the outer circumferential surface of the rear end. As shown in FIG. 4, the tip of a wire for rotationally driving 18 is fixed to the wire connection hole 25c. The wire 18 is inserted into a protective tube 19 and is connected to a motor 80 (refer to FIG. 13) in a hand operation unit 67. The motor 80 is controlled by a controller (not shown) so as to be forward rotated or backward rotated through an operation of a seesaw switch 79 of a hand operation unit 67.

As shown in FIGS. 1 and 3, a fixed ring 29 is mounted on the tip of the cam shaft 25. As shown FIG. 4, due to the fixed ring 29, the cam shaft 25 smoothly rotates without being inclined in the lens moving unit accommodating hole 34. In addition, since the locking flange 25d of the rear end side of the cam shaft 25 is locked to the locking ring 34a, the cam shaft 25 is not released out of the lens moving unit accommodating hole 34.

As shown in FIGS. 1 and 3, the first lens moving frame 26 includes a guide tube 26a, a lens frame 22a, and an arm 26b that connects the guide tube and the lens frame, and the guide tube 26a, the lens frame 22a, and the arm 26a are formed so as to be integrated. Similarly, the second lens moving frame 27 also includes a guide tube 27a, a lens frame 23a, and an arm 27b, and the guide tube 27a, the lens frame 23a, and the arm 27b are formed so as to be integrated. A first engagement pin 28a is mounted on the guide tube 26a of the first lens moving frame 26, and the tip of the engagement pin 28a enters into the first cam groove 25a. Moreover, a second engagement pin 28b is mounted on the guide tube 27a of the second lens moving frame 27, and the tip of the second engagement pin 28b enters into the second cam groove 25b.

If the cam shaft 25 is forward rotated or backward rotated by the motor 80 (refer to FIG. 13), the cam shaft 25 is rotated and displaced according to the rotating amount, and the first and second lens moving frames 26 and 27 move in the optical axis direction in the housing 13 via each of the engagement pins 28a and 28b through the rotation displacement.

Figure 5:
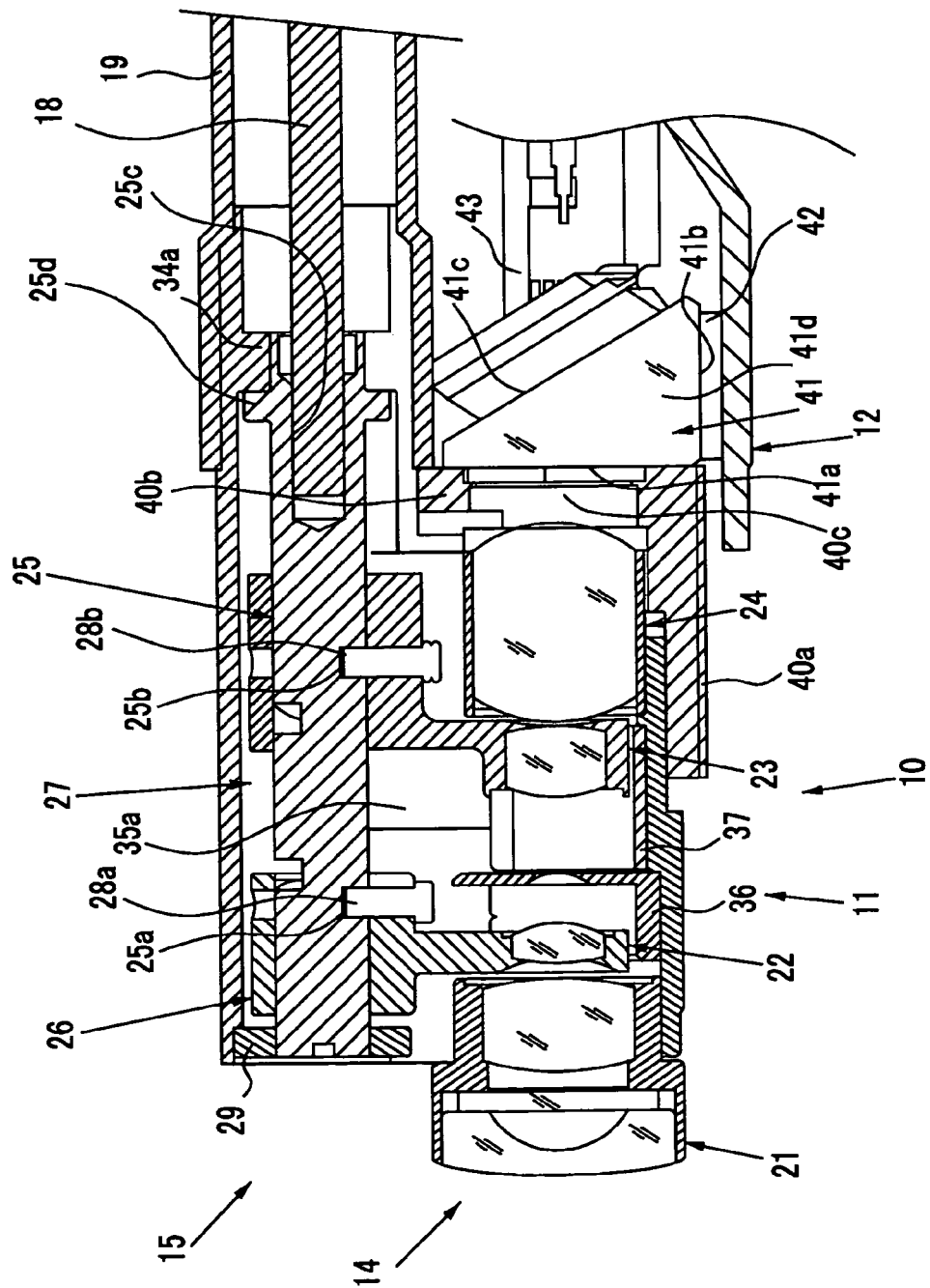
FIG. 5 is a main portion cross-sectional view of the camera module at an enlargement position.

FIGS. 4 and 5 illustrate switching of a focal distance of the photographic lens, FIG. 4 shows a standard position, and FIG. 5 shows an enlargement position. In the enlargement position, the first lens moving frame 26 moves further forward than the standard position, and the second lens moving frame 27 moves further backward than the standard position.

In order to smoothly move the first and second lens moving frames 26 and 27 in the optical axis direction through the rotation of the cam shaft 25, in the present embodiment, for example, each part is measured and parts combined within an interval of 3±3 μm are selected so that the thickness of the arms 26b and 27b of the first and second lens moving frames 26 and 27 and an interval of the distance between the slide guide surfaces of the slide holes when being fitted are within 3±3 μm, and the selected parts are used as a set.

As shown in FIG. 3, in the photographic lens accommodating hole 33, a first accommodating unit 33a that accommodates the first fixed lens 21 and the first movable lens 22, a second accommodating unit 33b that accommodates the second movable lens 23, and a third accommodating unit 33c that accommodates the second fixed lens 24 are formed in this order from the tip of the housing 13 toward the rear end. A ring protrusion 33d that is partitioned is formed between the second accommodating unit 33b and the third accommodating unit 33c. The second accommodating unit 33b is formed so that the inner diameter of the second accommodating unit is smaller than the inner diameter of the first accommodating unit 33a, and the second accommodating unit 33b and the third accommodating unit 33c are formed so that both inner diameters are the same as each other.

A second reflection protection tube 37 is accommodated in the second accommodating unit 33b. The second reflection protection tube 37 is formed in a tube shape and includes a slit 37a in the optical axis direction. The arm 27b of the second lens moving frame 27 enters the slit 37a, and the lens frame 23a of the second lens moving frame 27 enters the inner portion of the second reflection protection tube 37. The inner diameter of the second reflection protection tube 37 is formed so as to be slightly larger than the outer diameter of the lens frame 23a, and the lens frame 23a does not contact the inner circumferential surface of the tube 37 when the lens frame 23a moves in the tube 37.

A first reflection protection tube 36 is accommodated in the first accommodating unit 33a. The first reflection protection tube 36 is also formed so as to be similar to the second reflection protection tube 37 and includes a slit 36a. The difference between the first reflection protection tube 36 and the second reflection protection tube 37 is that a throttle plate 38 is integrally formed at the rear end of the first reflection protection tube 36. The rear end surface of the first reflection protection tube 36 is locked by a stepped surface 33e between the first accommodating unit 33a and the second accommodating unit 33b and is positioned when being accommodated. The lens frame 22a of the first lens moving frame 26 moves in the first reflection protection tube 36.

As shown in FIG. 3, in order to prevent occurrence of a flare, the lens frame 21a of the first fixed lens 21, the first lens moving frame 26 that integrally includes the lens frame 22a of the first movable lens 22, the second lens moving frame 27 that includes the lens frame 23a of the second movable lens 23, the lens frame 24a of the second fixed lens 24, and the first and second reflection protection tubes 36 and 37 are subjected to blackening processing, and a black layer 39 is formed on the surfaces of these. The blackening processing may use any one of well-known methods, and for example, the black layer 39 is formed according to chemical processing that uses a blackening processing solution. Moreover, since the black layer 39 appears as a cross-section having a slight thickness, the illustration showing the thickness is omitted. On the other hand, since the housing 13 has a complicated shape and is a minute part of about 7 mm×4 mm×15 mm as outer diameter dimensions, the black layer 39 having a desired thickness may not be formed in the inner circumferential surface of the housing, and the blackening processing is not performed.

Figure 6:
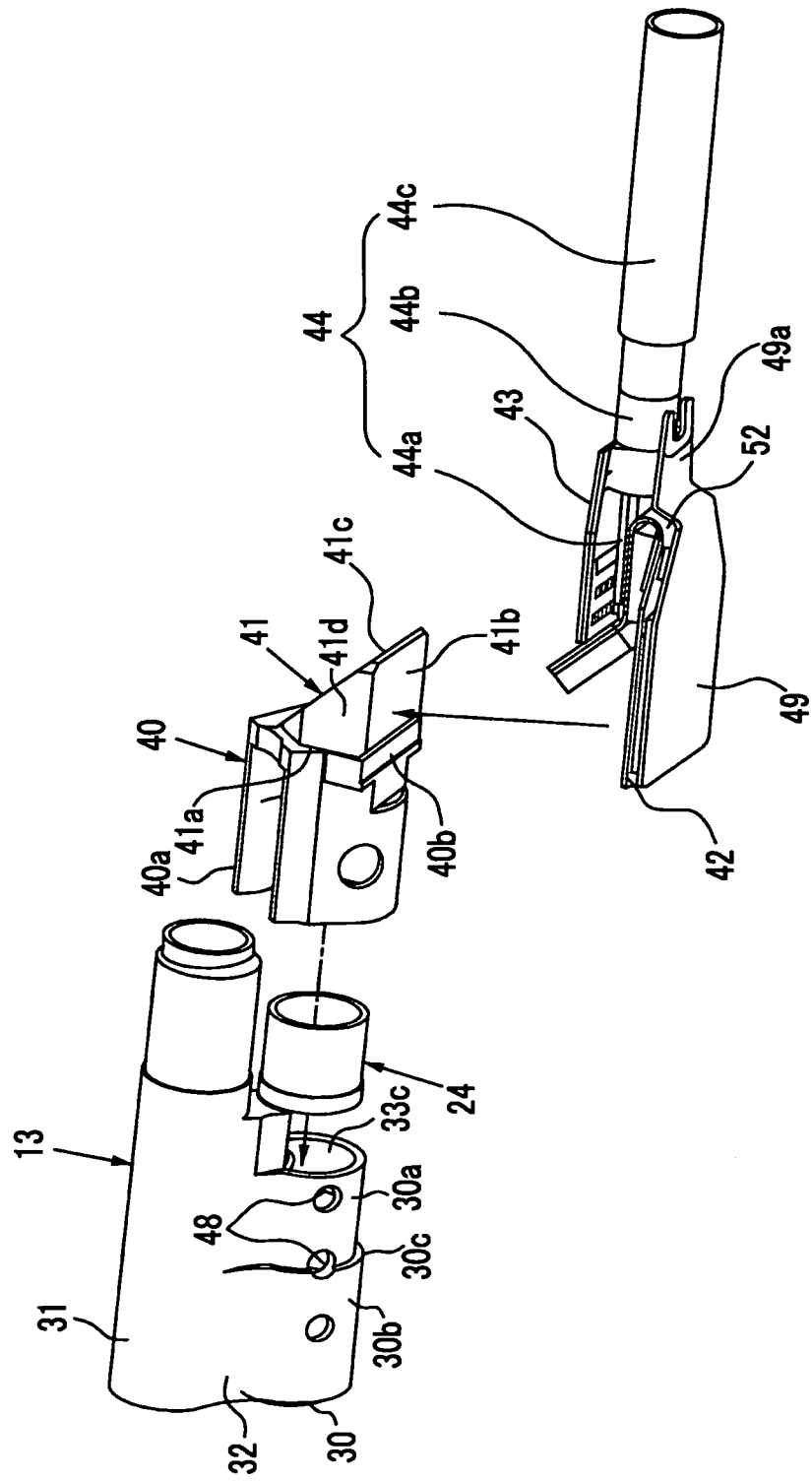
FIG. 6 is a perspective view in which electronic components such as the housing, a prism frame, and an image area sensor are shown in an exploded manner.
Figure 7:
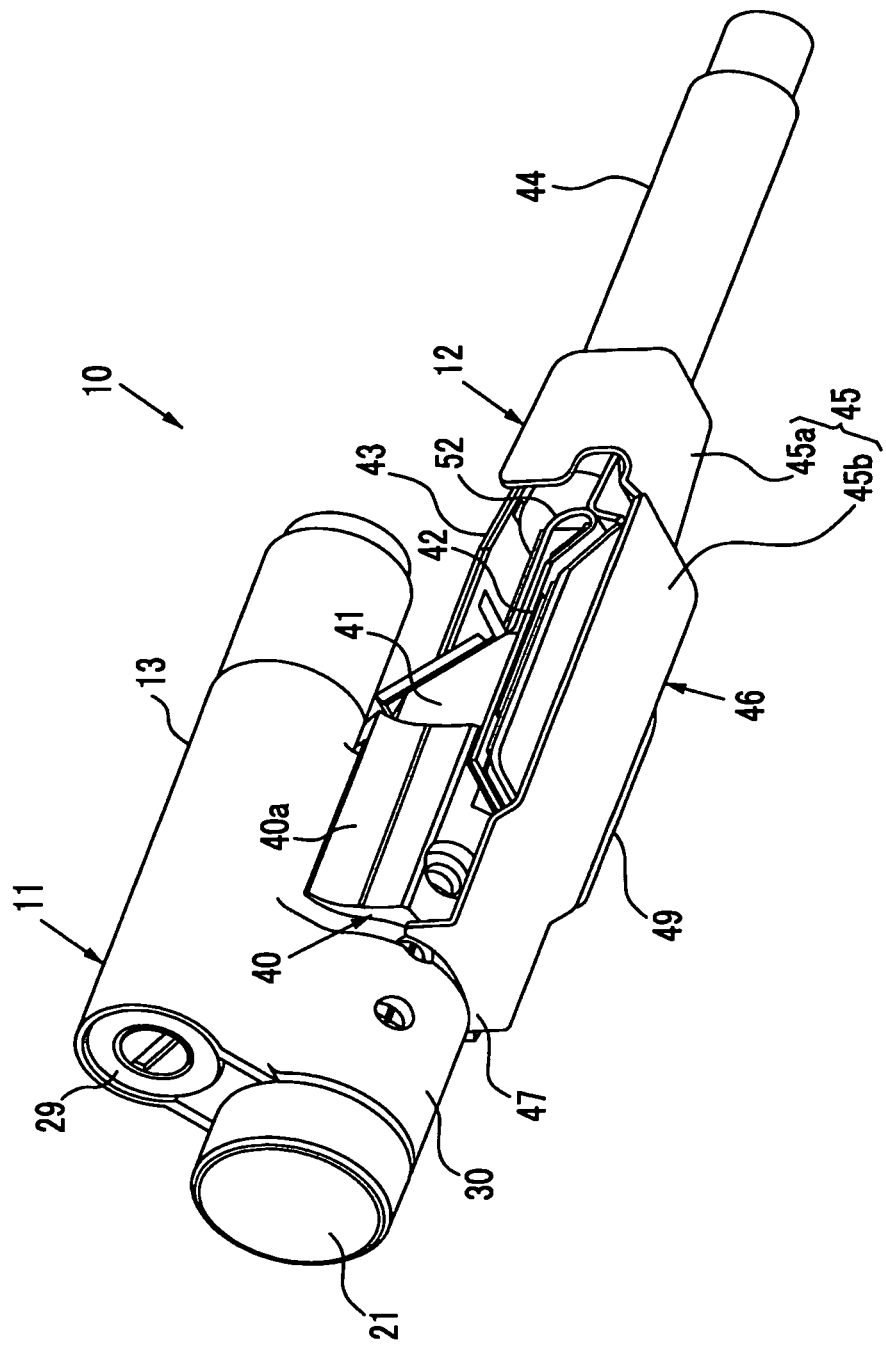
FIG. 7 is a perspective view showing the entire outline of the camera module.
Figure 8:
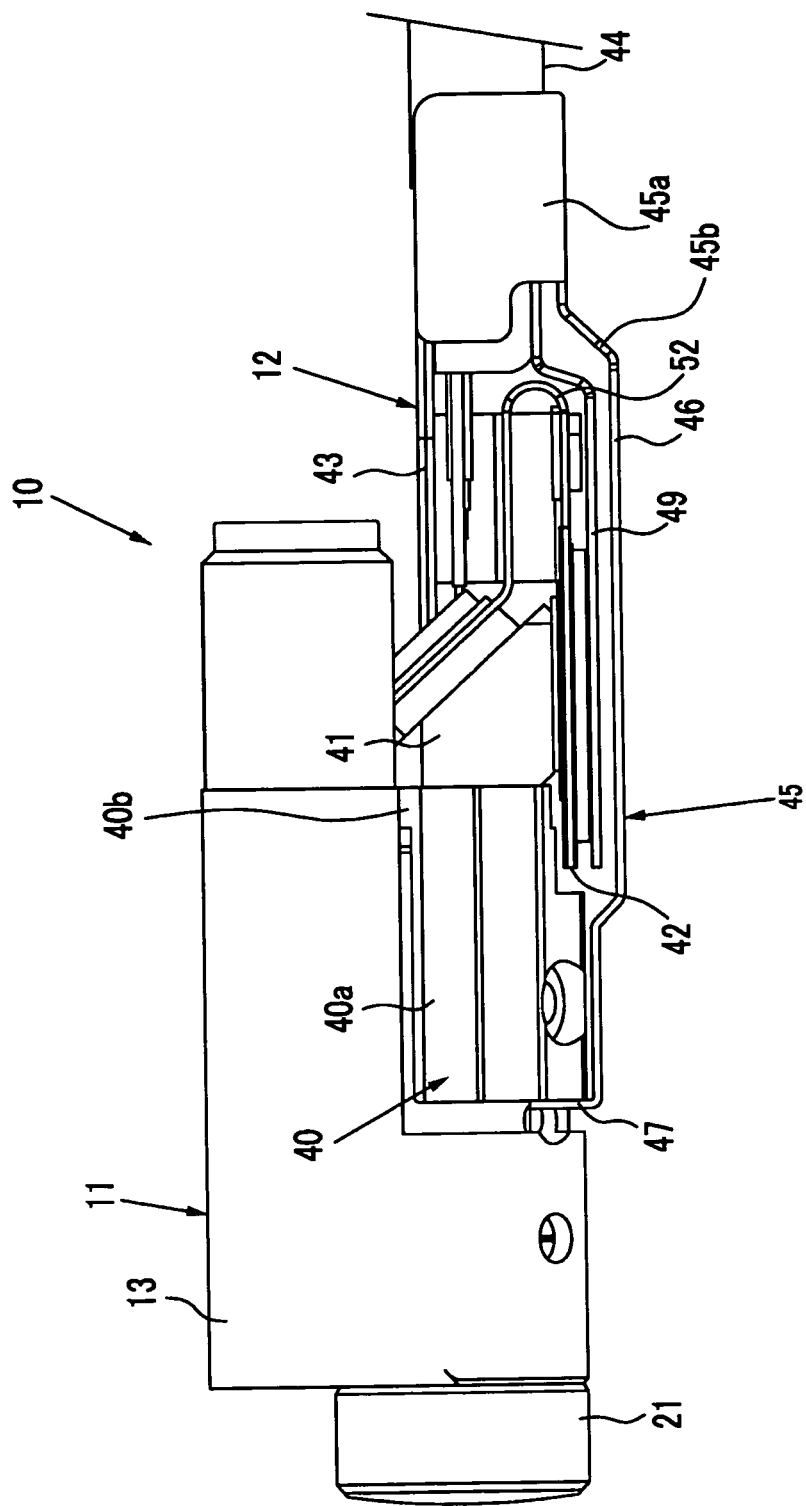
FIG. 8 is a side view of the entire outline of the camera module.

As shown in FIG. 6, since the second tube unit 31 accommodates the cam shaft 25, the second tube unit 31 is formed so as to be longer than the first tube unit 30. Moreover, mutual tips of the first and second tube units are arranged, the rear end of the second tube unit 31 protrudes further backward than the rear end of the first tube unit 30, and different levels between the first and second tube units are formed. A space is generated at the rear end side of the first tube unit 30 due to the different levels of the rear ends of the two tube units 30 and 31. As shown in FIGS. 7 and 8, an imaging unit 12 is mounted on the photographic lens unit 11 using the space, and a camera module 10 is configured.

As shown in FIG. 6, the outer diameter of the rear half 30a of the outer circumferential surface of the first tube unit 30 of the housing 13 is formed so as to be slightly larger than the diameter of the front half 30b of the outer circumferential surface, and a stepped surface 30c is formed between the front half 30b and the second half 30a. A prism holder 40 of the imaging unit 12 is mounted on the rear half 30a of the outer circumferential surface. In this way, the imaging unit 12 is disposed in the space of the rear end side of the first tube unit 30 via the prism holder 40, and thereby, the entire camera module 10 can be compactly configured.

As shown in FIGS. 7 and 8, the imaging unit 12 includes the prism holder 40, a prism 41, a CCD type image area sensor 42, a circuit substrate 43, a transmission cable 44, a cable connecting fitting 45, a heat dissipation plate 49, and a sealing agent (not shown) that seals wirings. Moreover, holes 48 that are formed on the housing 13 are required for adhesive material injection or inserting of screws when the reflection protection tubes 36 and 37 or the second fixed lens 24 are fixed into the photographic lens accommodating hole 33, and are provided as necessary.

As shown in FIG. 6, the prism holder 40 (prism holding frame) includes a mounting tube portion 40a and a prism mounting frame 40b (prism fixing surface). The prism 41 is configured of a rectangular prism that include five surfaces such as an incident surface 41a that intersects at right angles, an emitting surface 41b, a reflecting surface 41c that is configured of inclined surfaces, and both side surfaces 41d. The prism mounting frame 40b includes an opening 40c (refer to FIG. 4) through which incident light passes from the photographic lens 14, and a positioning piece 40d (refer to FIG. 10) is provided as the rear end surface of the prism mounting frame 40b. The side surfaces 41d of the prism 41 abut the positioning piece 40d, and thereby, the prism 41 is positioned. Therefore, it is not necessary to use a separate position regulating jig and the like when minute parts are assembled to one another, and the assembly can be simply performed with high accuracy. In addition, a plurality of positioning pieces may be provided as necessary, and in this case, positioning accuracy can be further enhanced.

As shown in FIGS. 7 and 8, the image area sensor 42 is mounted on the emitting surface 41b of the prism 41 through an adhesive material, and a circuit substrate 43 for driving the image area sensor 42 is mounted on the inclined surface of the prism 41 through an adhesive material. The circuit substrate 43 is connected to the image area sensor 42 via a flexible wiring circuit substrate 52, a wire connection (not shown), and the like. A wire (signal wire) 44a of the transmission cable 44 is connected to the circuit substrate 43. As shown in FIG. 6, the transmission cable 44 is configured of a plurality of wires 44a, a shield wire 44b that bundles and shields the wires 44a, and an outer cover 44c that covers the shield wire. In addition, the circuit substrate 43 may include a plurality of sub-boards in addition to a main substrate.

The heat dissipation plate 49 is fixed outside the image area sensor 42. A cable receiving unit 49a is formed on the rear end of the heat dissipation plate 49, and the cable receiving unit 49a is soldered to the shield wire of the transmission cable 44. The heat dissipation plate 49 dissipates heat from the image area sensor 42 to the transmission cable 44.

One end of the cable connecting fitting 45 at the same side as the cable receiving unit 49a of the heat dissipation plate 49 is fixed to the outer cover 44c of the transmission cable 44 through an adhesive material. The cable connecting fitting 45 includes a mounting frame unit 45a and a connection plate unit 45b. Both side portions of a metal plate are bent, and the mounting frame unit 45a is formed in a U shaped cross-section. An adhesive material is filled into the frame unit, and the frame unit is integrated with the transmission cable 44.

In the connection plate unit 45b, a flat plate is bent, an offset portion 46 is formed in the vicinity of the center of the plate unit, and a locking claw 47 is formed in the tip of the plate unit. The offset portion 46 is formed with an offset amount in which the image area sensor 42 or the heat dissipation plate 49 does not contact the offset portion. Thereby, the connection plate unit 45b which is a portion of the cable connecting fitting is close to the image area sensor 42, and is positioned so as to be parallel to the image area sensor. The locking claw 47 is formed so as to be bent by 90°, and the tip edge of the locking claw is formed in an arc form in accordance with the outer circumferential surface of the first tube unit 30 of the housing 13. An adhesive surface of the mounting tube portion 40a is interposed between the locking claw 47 and the offset portion 46, an adhesive material is filled therebetween, and thereby, the cable connecting fitting 45 is fixed to the prism holder 40. Since the offset portion 46 is provided according to a positional relationship between the image area sensor 42 and the outer circumferential surface of the mounting tube portion 40a of the prism holder 40, when the heat dissipation plate 49 that covers the image area sensor 42 from the outer circumferential surface of the mounting tube portion 40a does not protrude outside, the offset portion 46 is not necessary, and the connection plate unit 45b may be configured in a flat plate shape.

In order to protect the wire connection unit, wires, and the like that are covered by the cable connecting fitting 45 or the image area sensor 42 and the circuit substrate 43, a sealing agent (not shown) is injected therebetween as necessary and is hardened.

The cable connecting fitting 45 is a plate shape so as not to cover both sides of the image area sensor 42. Therefore, when the size of the image area sensor 42 is changed, although the size of the image area sensor 42 is increased according to the size change, the image area sensor does not contact the connection plate unit 45b, and thereby, a correspondence to the size change and the like of the image area sensor 42 is possible. In addition, since the heat dissipation plate 49 that protects the image area sensor 42 is not a frame shape but a plate shape, when the size of the image area sensor 42 is changed, the size change can be performed while maintaining the present structure.

In the above-described embodiment, the locking claw 47 is locked to the tip surface of the mounting tube portion 40a and is fixed. However, instead of the locking of the locking claw 47 to the tip surface, the locking claw may be locked to a step or a locking hole that is formed on the mounting tube portion 40a.

Figure 9:
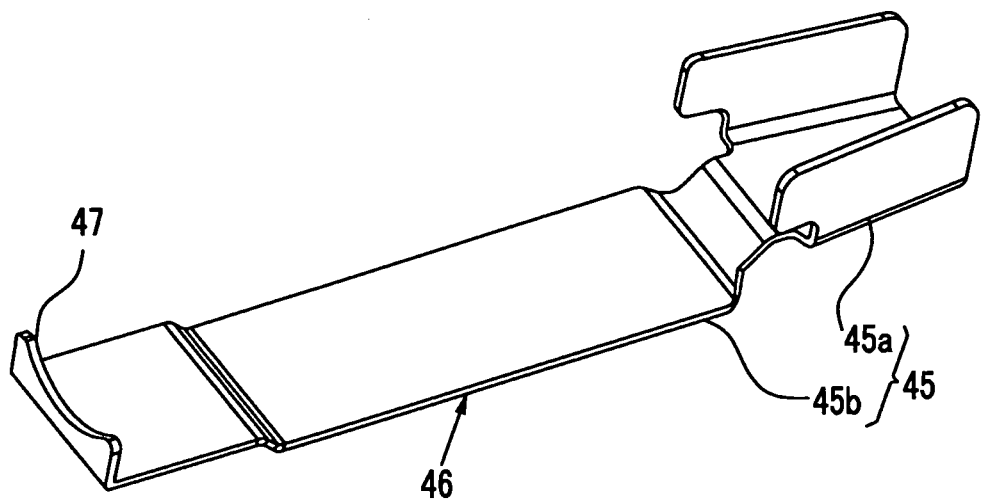
FIG. 9 is a perspective view showing a cable connecting fitting.
Figure 10:
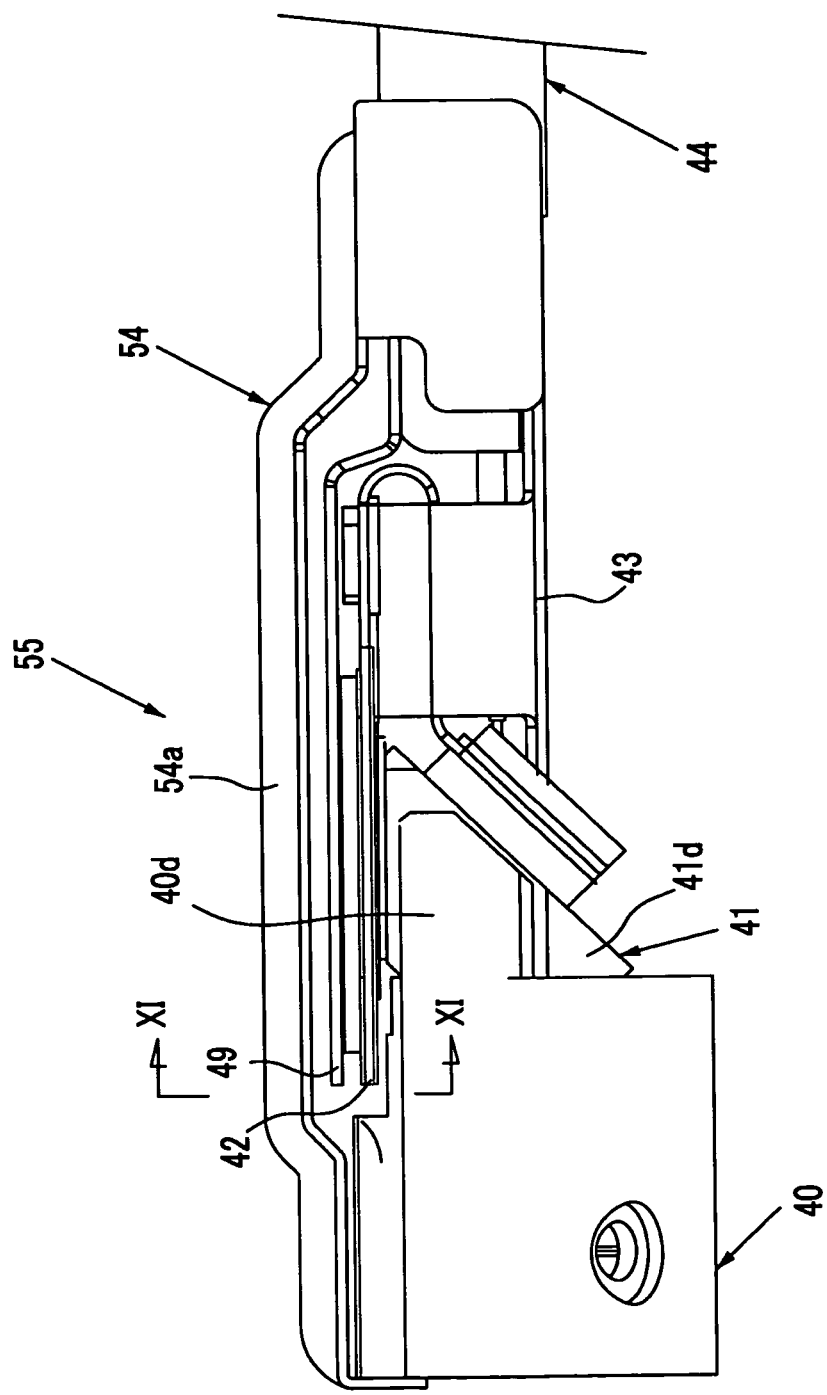
FIG. 10 is a side view showing a cable connecting fitting of another embodiment.
Figure 11:
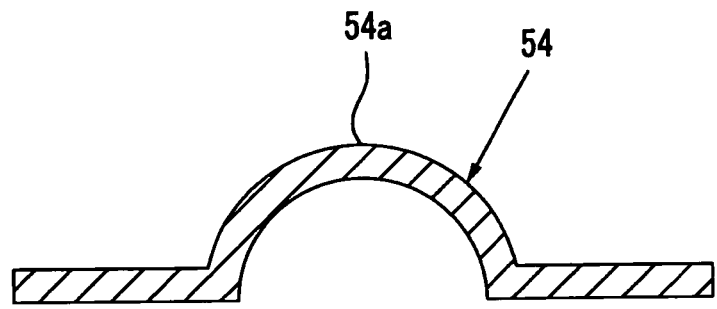
FIG. 11 is a cross-sectional view of the cable connecting fitting taken along a line XI-XI in FIG. 10.

FIGS. 10 and 11 show an imaging unit 55 that uses a cable connecting fitting 54 of another embodiment. In this cable connecting fitting 54, a protrusion 54a which is a reinforced rib is formed so as to protrude in the longitudinal direction of the cable connecting fitting 45 shown in FIG. 9. As the cross-sectional shape of the protrusion 54a, in addition to an arc shape shown in FIG. 11, a triangular form or other various shapes may be used.

Figure 12:
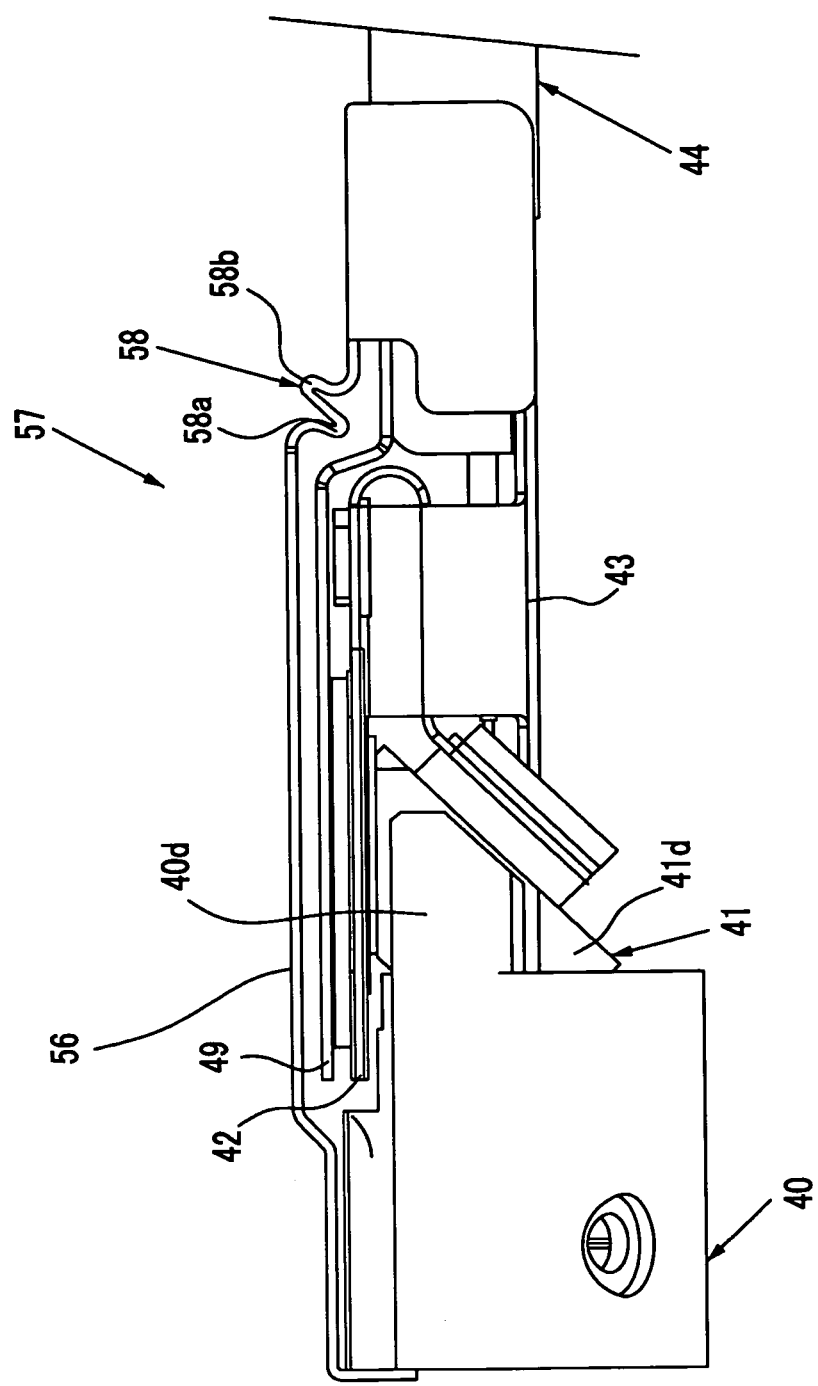
FIG. 12 is a side view showing a cable connecting fitting of still another embodiment.

FIG. 12 shows an imaging unit 57 that uses a cable connecting fitting 56 of still another embodiment. In this cable connecting fitting 56, a spring portion 58 is provided between the offset portion 46 of the cable connecting fitting 45 and the mounting frame unit 45a shown in FIG. 9. The spring portion 58 is bent in a bending line in the width direction perpendicular to the longitudinal direction of the connection plate unit 45b. For example, there may be four bending locations, and the bending portions may be a first bending portion 58a that is directed downward and a second bending portion 58b that is directed upward. However, the number of the bending portions or the bending shape can be appropriately changed. In this embodiment, even when the transmission cable 44 is pulled and a bending force is applied between the transmission cable 44 and the cable connecting fitting 56, since the spring portion 58 acts as an interference material or an absorbent material for the bending force, the bending force between the transmission cable 44 and the cable connecting fitting 56 is relieved, and thereby, occurrence of separation, cutting, or the like is prevented.

Figure 13:
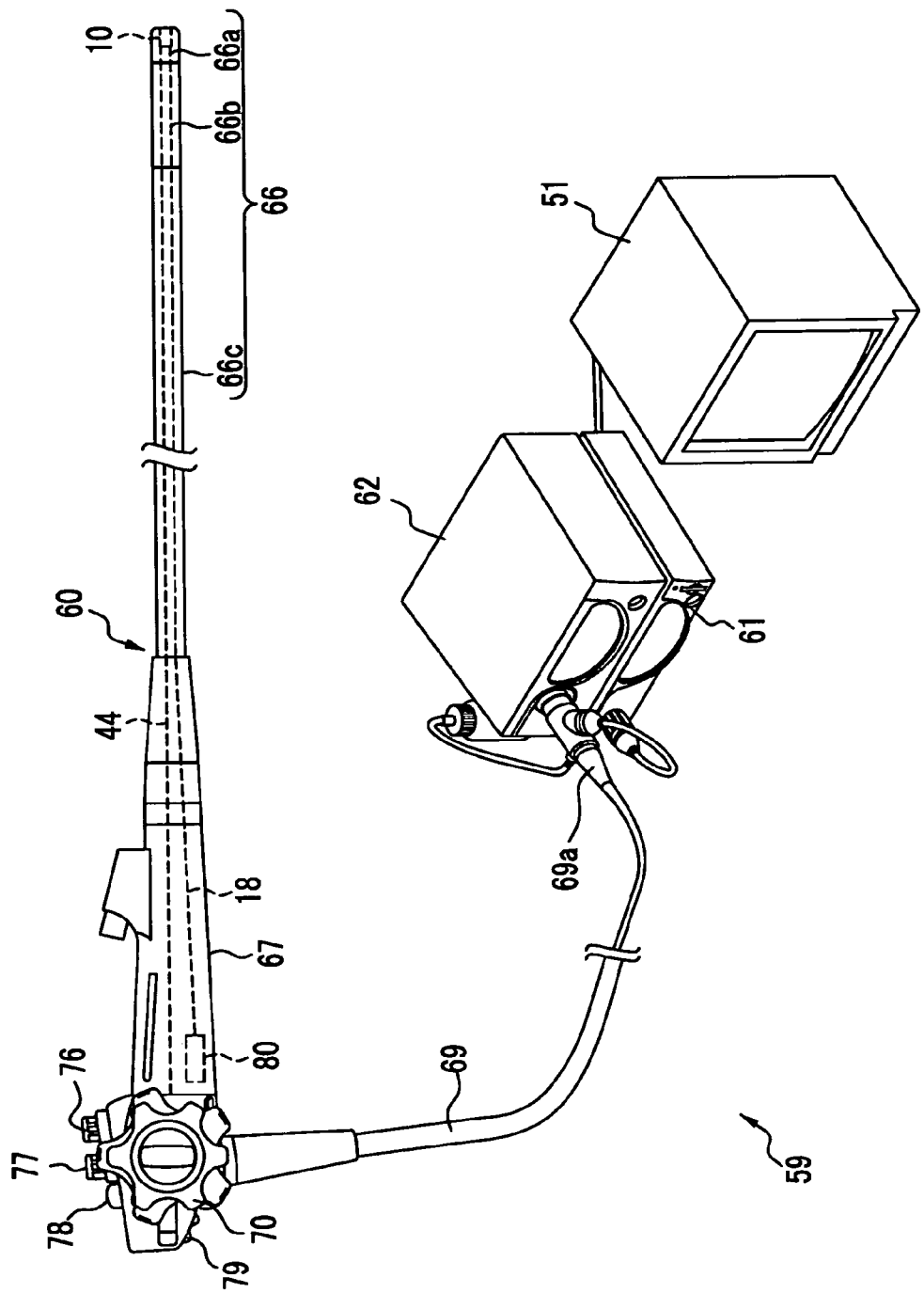
FIG. 13 is a perspective view showing a configuration of an electronic endoscope system.

As shown in FIG. 13, the camera module 10 that is configured as described above is mounted on an insert unit 66 of an electronic endoscope 60. An electronic endoscope system 59 includes the electronic endoscope 60, a processor device 61, and a light source device 62. The electronic endoscope 60 includes the flexible insert unit 66 that is inserted into a body cavity of a patient, a hand operation unit 67 that is provided so as to extend to the base end of the insert unit 66, a connector 69a that is connected to the processor device 61 and the light source device 62, and a universal cord 69 that performs connection between the hand operation unit 67 and the connector 69a.

Figure 14:
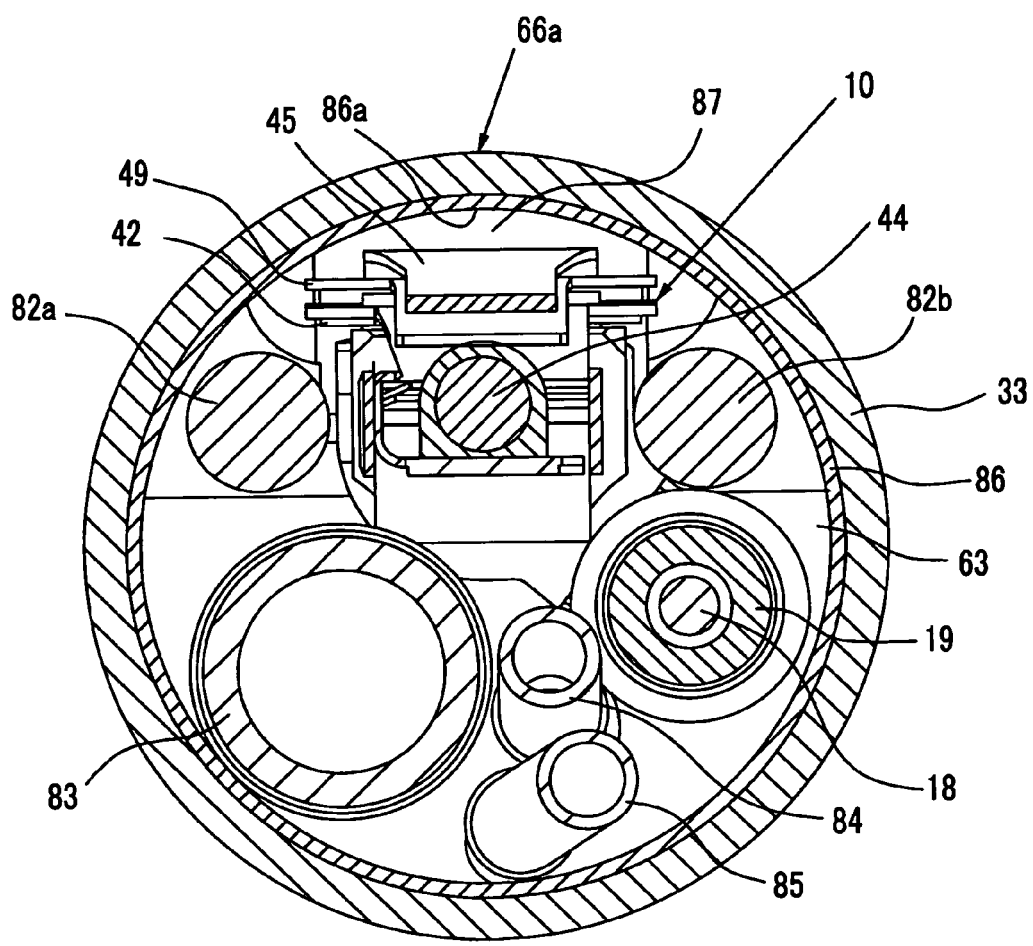
FIG. 14 is a cross-sectional view of a distal end hard portion of an endoscope.

The insert unit 66 includes a distal end hard portion 66a, a curved portion 66b, and a soft portion 66c in this order from the tip. In FIG. 14 that shows the cross-sectional shape of the distal end hard portion 66a, a distal end cap made of a soft resin is covered on a distal end main body 63 made of a rigid resin, the distal end main body 63 and a distal end tube 86 made of a metal of the curved portion 66b that extends to the main body 63 are covered by a tube, and thereby, the distal end hard portion 66a is configured.

In the distal end main body 63, light guides 82a and 82b, a forceps channel 83, an air supply tube 84, and a water supply tube 85 are mounted in addition to the camera module 10 of the present invention. The housing 13 enters a mounting hole that is formed on the distal end main body 63 and is screwed, and thereby, the camera module 10 is fixed to the distal end main body 63. The image area sensor 42 of the camera module 10 is disposed so as to be close to the inner circumferential surface of the distal end main body 63, to be exact, the inner circumferential surface of the distal end tube 86 made of a metal of the curved portion 66b. Thereby, since the photographic lens unit is disposed between the light guides 82a and 82b and the wire 18 for driving the cam shaft is disposed between the air supply tube 84 and the light guide 82b in the distal end hard portion 66a, intervals between built-in members are decreased, and the built-in members can be efficiently disposed.

Particularly, since the image area sensor 42 is disposed in the vicinity of the cylinder of the distal end tube 86, a space is formed between the image area sensor 42 and the inner circumferential surface 86a of the distal end tube 86, and the space becomes a dead space 87. In the present invention, since the cable connecting fitting 45 is disposed in the dead space 87, the dead space 87 can be effectively used, and accordingly, a decrease of the diameter of the insert unit 66 can be improved. Moreover, since the protrusion 54a or the spring portion 58 in the second and third embodiments is formed using the dead space, the protrusion or the spring portion can reinforce the cable connecting fittings 54 and 56 or can be used as a buffer material.

The curved portion 66b includes a unit in which each joint ring is connected by pins, and the entirety of the curved portion is bent. The curved portion 66b is curved at an arbitrary angle in vertical and horizontal directions by rotation operation of an angle knob 70 of the hand operation unit 67.

Thereby, the distal end hard portion 66a is directed in a desired direction in a body cavity, and an observation portion in the body cavity can be radiographed by the camera module 10. The soft portion 66c is a portion having a small diameter and a long shape which is connected between the hand operation unit 67 and the curved portion 66b, and has flexibility.

Figure 15:
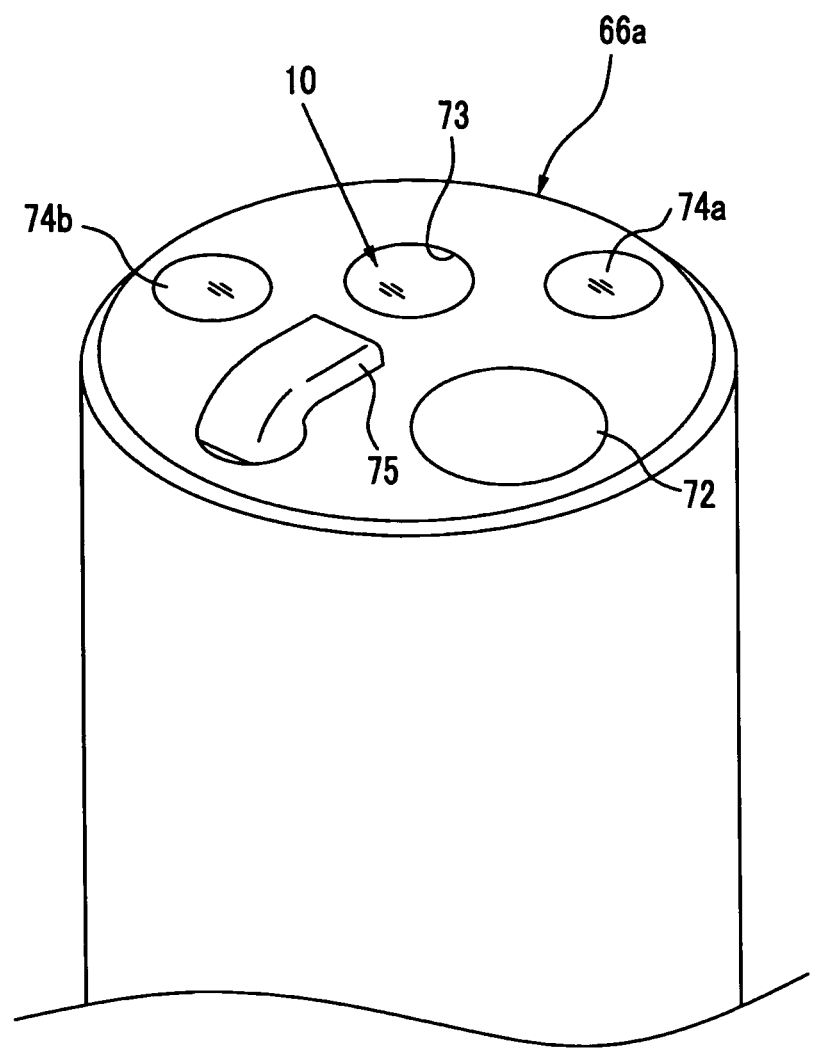
FIG. 15 is a perspective view showing a distal end hard portion of an electronic endoscope.

As shown in FIG. 15, an observation window 73, illumination windows 74a and 74b, and an air and water supply nozzle 75 are provided on the tip surface of the distal end hard portion 66a in addition to a forceps outlet 72. The lens 21 of the camera module 10 of the present invention is disposed on the observation window 73, the light guides 82a and 82b are connected to the illumination windows 74a and 74b, and the air supply tube 84 and the water supply tube 85 are connected to the air and water supply nozzle 75. In addition, a water jet outlet, other nozzles, and the like are provided as necessary.

The hand operation unit 67 includes various operating members such as the angle knob 70, an air and water supply button 76, a suction button 77, a release button 78, and a seesaw switch for zoom operation 79. The angle knob 70 is operated so as to rotate, and the distal end hard portion 66a of the insert unit 66 is bent in vertical and horizontal directions. The air and water supply button 76 is operated so as to be pressed, and air or water from the air and water supply nozzle 75 is ejected. The suction button 77 is operated so as to be pressed, and objects to be suctioned such as liquid or tissue in the body is suctioned from the forceps outlet 72. The release button 78 is operated so as to be pressed, and the observed image from the camera module 10 is recorded to a still image. The seesaw switch 79 rotates the motor 80 forward or backward, the rotation is transmitted to the cam shaft 25 via the wire 18, and the photographic lens 14 is changed to standard photographing or enlargement photographing.

The processor device 61 is electrically connected to the light source device 62 and generally controls the operation of the electronic endoscope system 59. The processor device 61 feeds electric power to the electronic endoscope 60 via the transmission cable 44 that is inserted into the universal cord 69 or the insert unit 66, and controls driving of the camera module 10 of the distal end hard portion 66a. In addition, the processor device 61 receives signals from the camera module 10 via the transmission cable 44, performs various processings, and generates image data. A monitor 81 is connected to the processor device 61. The monitor 81 displays observed images based on the image data from the processor device 61.

Moreover, in the above-described embodiments, the example in which two movable lenses 22 and 23 are used as the photographic lens unit 11 is described. However, there may be one or more movable lenses. In addition, instead of performing variable magnification or focusing the movable lens, the present invention may be applied to a photographic lens unit having a fixed focus. Moreover, in the above-described embodiments, the example in which the present invention is applied to a medical endoscope is described. However, the present invention may be also applied to an industrial endoscope.

What is claimed is:
1. An endoscope comprising:
an insert unit that includes an end hard portion;
a camera module formed in the end hard portion;
a photographic lens unit that includes a photographic lens and a housing holding the photographic lens;
a prism that includes an incident surface to which photographing light from the photographic lens is incident, a reflecting surface at which the photographing light inci- dent to the incident surface is reflected, and an emitting surface that emits the photographing light reflected at the reflecting surface;

a prism holding frame that includes a mounting tube portion mounted on one end of the housing, an opening through which incident light of the incident surface of the prism passes, and a prism fixing surface to which a peripheral edge of the incident surface of the prism is fixed;

an image area sensor that is mounted on the emitting surface of the prism;

a circuit substrate that drives the image area sensor;

a transmission cable that includes wires connected to the circuit substrate and an outer cover that bundles and protects the wires; and a cable connecting fitting which is close to the image area sensor and disposed so as to be parallel to the image area sensor, and comprising:

a connection plate unit comprising a plate and being open on both sides in a direction perpendicular to the optical axis of the image area sensor; and a mounting frame unit disposed on one end of the connection plate unit and fixed to the outer cover of the transmission cable, an other end of the connection plate unit being mounted on the mounting tube portion, wherein a width of the connection plate unit in a direction orthogonal to the optical axis of the cable connecting fitting is less than a width of the connection plate unit in the direction perpendicular to the optical axis of the image area sensor, and the connection plate unit is disposed in a vicinity of a cylinder of the end hard portion.

2. The endoscope according to claim 1,
wherein the other end of the connection plate unit includes a locking claw locked to a surface of a tip of the mounting tube portion.

3. The endoscope according to claim 2,
wherein the other end of the connection plate unit is fixed to the mounting tube portion.

4. The endoscope according to claim 3,
wherein the cable connecting fitting includes a protrusion for reinforcement on the opposite side of the mounting surface of the image area sensor that is provided from one end of the cable connecting fitting to an other end of the cable connecting fitting.

5. The endoscope according to claim 3,
wherein the cable connecting fitting includes a spring portion that is bent in a width direction perpendicular to a longitudinal direction of the cable connecting fitting.

6. The endoscope according to claim 2,
wherein the cable connecting fitting includes a protrusion for reinforcement on the opposite side of the mounting surface of the image area sensor that is provided from one end of the cable connecting fitting to an other end of the cable connecting fitting.

7. The endoscope according to claim 2,
wherein the cable connecting fitting includes a spring portion that is bent in a width direction perpendicular to a longitudinal direction of the cable connecting fitting.

8. The endoscope according to claim 1,
wherein an end of the transmission cable is fixed to the mounting tube portion.

9. The endoscope according to claim 8,
wherein the cable connecting fitting includes a protrusion for reinforcement on the opposite side of the mounting surface of the image area sensor that is provided from one end of the cable connecting fitting to an other end of the cable connecting fitting.

10. The endoscope according to claim 8,
wherein the cable connecting fitting includes a spring portion that is bent in a width direction perpendicular to a longitudinal direction of the cable connecting fitting.

11. The endoscope according to claim 1,
wherein the cable connecting fitting includes a protrusion for reinforcement on an opposite side of a mounting surface of the image area sensor that is provided from one end of the cable connecting fitting to an other end of the cable connecting fitting.

12. The endoscope according to claim 1,
wherein the cable connecting fitting includes a spring portion that is bent in a width direction perpendicular to a longitudinal direction of the cable connecting fitting.

13. The endoscope according to claim 1, wherein the photographic lens unit comprises:
the photographic lens which includes a movable lens movable in an optical axis direction;
a lens moving unit including a lens moving frame for holding the movable lens, and being movable in the optical axis direction; and
a housing including side-by-side in a direction perpendicular to the optical axis:
a photographic lens accommodating hole accommodating the photographic lens;
a lens moving unit accommodating hole accommodating the lens moving unit; and
a slide hole that connects the photographic lens accommodating hole and the lens moving unit accommodating hole, and wherein the mounting tube portion is attached to one end of the housing around the lens accommodating hole.

14. The endoscope according to claim 13, wherein the housing includes a first tube unit including the photographic lens accommodating hole, a second tube unit having the lens moving unit accommodating hole and a connection unit connecting side by side in the direction perpendicular to the tube axial of the first tube unit and the second tube unit.

15. The endoscope according to claim 14, wherein a length of the first tube unit is less than a length of the second tube unit in the optical axis direction and the first tube unit is aligned with the tip of the second tube unit, and a stepped portion is formed between an end of the first tube unit and the second tube unit and the prism holding frame and the image area sensor are attached on the stepped portion.

16. The endoscope according to claim 15, wherein an outer diameter of the second tube unit is less than an outer diameter of the first tube unit, and
wherein the first and second tube units form a figure eight shape when viewed from the tube axial direction.

17. The endoscope according to claim 1, wherein the insert unit further comprises a curved portion connected to the end hard portion, and a soft portion connected to the curved portion.

* * * * *